United States Patent [19]

Kobayashi et al.

[11] Patent Number: 5,334,512
[45] Date of Patent: Aug. 2, 1994

[54] FATTY ACID SUPPLEMENTED MEDIUM FOR RECOMBINANT PRODUCTION OF HUMAN SERUM ALBUMIN BY YEAST

[75] Inventors: Kaoru Kobayashi; Shinobu Kuwae; Tomoshi Ooya; Hirotoshi Fukutsuka; Akinori Sumi; Wataru Ohtani; Takao Ohmura; Kazumasa Yokoyama, all of Hirakata, Japan

[73] Assignee: The Green Cross Corporation, Osaka, Japan

[21] Appl. No.: 854,841

[22] Filed: Mar. 20, 1992

[30] Foreign Application Priority Data

Mar. 20, 1991 [JP] Japan .................. 3-081719

[51] Int. Cl.$^5$ .......... C12N 1/19; C12N 1/38; C12N 15/81; C12P 21/02
[52] U.S. Cl. .................. 435/69.6; 435/69.1; 435/171; 435/254.2; 435/254.21; 435/254.23; 935/37
[58] Field of Search ............ 435/69.1, 69.6, 171, 435/255; 935/37

[56] References Cited

U.S. PATENT DOCUMENTS 5,024,947  6/1991  Inlow et al. .................. 435/70.1

FOREIGN PATENT DOCUMENTS

| | | |
|---|---|---|
| 073646 | 8/1982 | European Pat. Off. . |
| 079739 | 11/1982 | European Pat. Off. . |
| 123544A | 4/1984 | European Pat. Off. . |
| 206733A | 6/1986 | European Pat. Off. . |
| 229712A | 1/1987 | European Pat. Off. . |
| 248637A | 6/1987 | European Pat. Off. . |
| 251744A | 6/1987 | European Pat. Off. . |
| 319641A | 5/1988 | European Pat. Off. . |
| 329127A | 2/1989 | European Pat. Off. . |
| 344459A | 4/1989 | European Pat. Off. . |
| 399455A | 5/1990 | European Pat. Off. . |
| 409156A | 7/1990 | European Pat. Off. . |
| 420007A | 9/1990 | European Pat. Off. . |
| 1060370 | 3/1989 | Japan . |

OTHER PUBLICATIONS

Weiss et al., "Replication of *Heliothis zea* Baculovirui . . .", In Vitro 20: 271, Abst #125, Mar. 1984.

Chisholm et al., "Molecular and Genetic Approval to Enhancing Protein Secretion", *Meth. Enzymol.* 185:471–482, 1991.

*Primary Examiner*—Robert A. Wax
*Assistant Examiner*—Stephen Walsh
*Attorney, Agent, or Firm*—Sughrue, Mion, Zinn, Macpeak & Seas

[57] ABSTRACT

A method for producing human serum albumin which comprises cultivating a human serum albumin-producing host prepared by genetic engineering, in a medium containing a fatty acid having 10 to 26 carbon atoms, or its salt, and a method for cultivating the host. HSA production can be greatly increased by the present invention.

5 Claims, No Drawings

5,334,512

FATTY ACID SUPPLEMENTED MEDIUM FOR RECOMBINANT PRODUCTION OF HUMAN SERUM ALBUMIN BY YEAST

FIELD OF THE INVENTION

The present invention relates to improvement of a method for producing human serum albumin (hereinafter referred to as HSA), which comprises cultivating a host transformed by genetic engineering.

BACKGROUND OF THE INVENTION

HSA is a major protein component of plasma and has been used as a medicine for the treatment of, for example, massive bleeding, shocks, burn, hypoproteinosis, fetal erythroblastosis and so on.

At present, HSA is produced mainly from fractions of collected blood. However, this production method is uneconomical and besides, the supply of the blood from which the HSA is produced is not always assured. Moreover, blood can pose problems since it contains undesirable substances, such as hepatitis virus.

In recent years, production of various useful polypeptides by microorganisms or cells has become possible with the advent of recombinant DNA technology, and studies and developments of large-scale production of HSA by genetic engineering have been made. However, the yield of HSA is low and an industrial production technique which permits HSA production at a low cost with high purity remains to be established.

SUMMARY OF THE INVENTION

In view of the technical background as mentioned above, the present invention aims at increasing the production amount of HSA by way of improvement of culture conditions.

DETAILED DESCRIPTION OF THE INVENTION

The present invention relates to a production method of HSA which comprises addition of a higher fatty acid having 10–26 carbon atoms or its salt to a culture medium when culturing an HSA-producing host prepared by genetic engineering. In this way, the production of HSA can be increased greatly.

The present invention also relates to a method for culturing a host prepared by genetic engineering and capable of producing human serum albumin, which comprises culturing in a medium supplemented with a fatty acid having 10 to 26 carbon atoms or its salt.

The HSA producing host to be used in the present invention, which is prepared by genetic engineering, is subject to no particular limitation as long as it is prepared by genetic engineering, and those disclosed in known literature or those to be developed in the future appropriately can be used. Specific examples of suitable hosts imparted with HSA producibility by genetic engineering include *Escherichia coli*, yeasts, *Bacillus subtilis* etc., and animal cells. Particularly in the present invention, the use of a yeast, specifically the genus Saccharomyces or the genus Pichia, as a host is desirable. Also, auxotrophic strains or antibiotic sensitive strains can be used. In addition, the *Saccharomyces cerevisiae* AH22 strain or *Pichia pastoris* GTS115 strain preferably can be used.

The method for the preparation of these HSA-producing hosts and the production method for HSA by the cultivation of a host, and the method for the separation and harvesting of HSA from cultures may be known methods or methods analogous thereto. For example, the methods for the preparation of HSA-producing host (or HSA-producing strain) include a method wherein a known human serum albumin gene is used (European Patent Publication Nos. 73646, 79739 and 206733), a method wherein a synthesized signal sequence is used (European Patent Publication No. 329127), a method wherein a serum albumin signal sequence is used (European Patent Publication No. 319641), a method wherein a recombinant plasmid is incorporated on a chromosome (European Patent Publication No. 399455), a method wherein hosts are fused (European Patent Publication No. 409156), a method wherein mutation is caused in a medium containing methanol, a method wherein a variant $AOX_2$ promoter (obtained by modifying a natural $AOX_2$ promoter, such as by partial deletion, substitution in or addition to the base sequence to improve activity as a promoter) is used, a production of HSA with yeast (European Patent Publication Nos. 123544, 248637 and 251744), a production of HSA with Pichia (European Patent Publication No. 344459) and the like.

Of the methods mentioned above, the method wherein mutation is caused in a medium containing methanol comprises the following steps. That is, a plasmid having a transcription unit where HSA is expressed under the control of an $AOX_1$ promoter is introduced into a suitable host, preferably a Pichia yeast, specifically into an $AOX_1$ gene region of the GTS115 strain (NRRL accession No. Y-15851) by a conventional method to obtain a transformant (see European Patent Publication No. 344459). This transformant shows poor growth in a medium containing methanol. Then, this transformant is grown in a medium containing methanol to cause mutation, and only viable strains are collected. The methanol concentration is about 0.0001–5%. The medium may be artificial or natural and incubation is conducted at 15°–40° C. for 1–1000 hours.

The methods for cultivating an HSA-producing host, namely, an HSA production method, include a method wherein a fed batch is used, besides the methods described in the above publications.

The methods for separating, harvesting, and purifying HSA include inactivation of protease by heat treatment (European Patent Application No. 420007) and the staining prohibition method comprising various chromatography treatments, besides the methods described in the above publications.

The medium to be used for cultivating a transformed host is a medium known in the field which has been supplemented with a fatty acid having 10–26 carbon atoms, or its salt, and the cultivation is conducted by a conventional method. The medium may be synthesized or natural, with preference given to liquid medium. For example, a synthesized medium may contain various sugars as carbon sources, urea, ammonium salt, nitrate etc. as nitrogen sources, various vitamins and nucleotide as micronutrients, and Mg, Ca, Fe, Na, K, Mn, Co, Cu etc. as inorganic salts, and exemplified by YNB liquid medium (0.7% yeast nitrogen base (Difco), 2% glucose). Examples of the natural medium include YPD liquid medium (1% yeast extract (Difco), 2% Bactopeptone (Difco), 2% glucose). The pH of the medium may be neutral, weak basic or weak acidic. When the host utilizes methanol, a medium containing methanol can be used. In this case, the methanol concentration is about 0.01–5%.

The incubation temperature is preferably 15°–40° C. (20°–30° C. for yeasts and 20°–37° C. for bacteria). The incubation is conducted for about 1 to 1000 hours, by allowing to stand, shaking or stirring, under aeration by batch culture, semibatch culture or continuous culture. Preculture in advance of the culture is preferable, wherein the medium used is, for example, YNB liquid medium or YPD liquid medium. The preculture is conducted for 10 to 100 hours at 30° C. for yeasts and 37° C. for bacteria.

The fatty acid to be used in the present invention is exemplified by those having 10 to 26, preferably 14 to 20, more preferably 14 to 18 carbon atoms, such as saturated or unsaturated fatty acids (e.g. myristic acid, palmitic acid, palmitoleic acid, oleic acid, t-vaccenic acid, linoleic acid and arachidonic acid). As the salts of these fatty acids, exemplified are alkali metal salts, such as sodium salt and potassium salt, alkaline earth metal salts, such as calcium salt, and organic amine salts.

The fatty acid is added to the medium at a concentration of about 0.005–0.4% (w/v), with preference given to 0.01–0.2%. When it is added at a concentration of less than 0.005%, desired effects cannot be obtained, and when added at a concentration of more than 0.4%, production may decrease. While the fatty acid generally is added to the medium in an appropriate amount before the initiation of the incubation, it may be added at the initial stage of the incubation.

After the termination of the incubation, HSA can be separated and purified by a known method from culture filtrate, fungi or cells.

The present invention is described in detail in the following illustrating Examples.

EXAMPLE 1

1. Strain to be used: *Pichia pastoris* GCP101

PC4130 can be obtained by replacing the $AOX_1$ gene region of *Pichia pastoris* GTS115 (his 4) (NRRL Y-15851) with a fraction cleaved with Not 1 of plasmid pPGP1 having a transcription unit where HSA is expressed under the control of $AOX_1$ promoter, by the method as described in European Patent Publication No. 344459. Due to the absence of the $AOX_1$ gene, this strain shows poor growth in a medium containing methanol as a carbon source (Mut-strain).

PC4130 was inoculated into 3 ml of YPD medium (1% yeast extract, 2% Bacto-peptone, 2% glucose) and 24 hours later, it was inoculated into 50 ml of YPD medium at a concentration with an initial $OD_{540}$ of 0.1. After incubation at 30° C. for 3 days, it was inoculated into 50 ml of YPD medium at a concentration with an initial $OD_{540}$ of 0.1. The same subculture was repeated every three days. At every subculture, the cells were diluted with sterilized water to make the cell concentration $10^7$ cells/plate and coated on a 2% MeOH-YNB w/o a. a. plate (0.7% yeast nitrogen base without amino acid, 2% methanol, 1.5% agar powder). After incubation at 30° C. for 5 days, presence or absence of colonies was assessed. Twenty colonies were formed on a 2% MeOH-YNB w/o a. a. plate which had been coated with cells after 12 days subculture. A Mut-strain hardly grew on this plate, but Mut+ strains could grow. That is, colony formation on this plate indicates increased utilization of methanol, and that a strain converted to Mut+ could be obtained. One of the colonies formed was appropriately diluted with sterilized water, and expanded on a 2% MeOH-YNB w/o a. a. plate to yield a single colony which was named GCP101.

2. Medium a) Medium for preculture

Bacto-Yeast Nitrogen Base (Difco, 6.7 g) was dissolved in water to make 100 ml, and 10×YNB, which was sterilized and filtered, 20% glucose which was sterilized in an autoclave, and sterilized water were mixed at the ratio of 1:1:8 (v) and used.

b) Medium for culture

Various fatty acids as shown in Table 2 were added to a medium containing methanol and glycerol as carbon sources (Table 1), and used as a medium for the culture (pH 6.0).

TABLE 1

| Component | Concentration (1/l) | |
|---|---|---|
| methanol | 40 | ml |
| glycerol | 1,000 | mg |
| ammonium acetate | 5,000 | mg |
| $KH_2PO_4$ | 10,000 | mg |
| $CaCl_2\ 2H_2O$ | 100 | mg |
| KCl | 2,000 | mg |
| NaCl | 100 | mg |
| $MgSO_4\ 7H_2O$ | 2,000 | mg |
| $ZnSO_4\ 7H_2O$ | 100 | mg |
| $CuSO_4\ 5H_2O$ | 5 | mg |
| $FeCl_3\ 6H_2O$ | 100 | mg |
| biotin | 0.1 | mg |
| vitamin $B_1$ | 10 | mg |
| vitamin $B_6$ | 1 | mg |
| pantothenic acid sodium | 10 | mg |
| inositol | 50 | mg |

3. Method of culture a) preculture

One ml of 20% glycerol stored frozen in culture in a vial was inoculated into 100 ml of YNB broth and the broth was subjected to shaking culture in a 300 ml-Erlenmeyer flask equipped with a baffle at 30° C. for 24 hours.

b) Culture

After 100 ml of the preculture was subjected to centrifugal harvesting, it was suspended in 10 ml of sterilized water. The cell suspension (0.5 ml) was inoculated into 50 ml of the culture. The culture (50 ml) was dispensed to a 300 ml-Erlenmeyer flask equipped with a baffle and subjected to shaking culture at 30° C. and 125 rpm for 120 hours.

The changes of HSA production amount and cell amount resulting from the cultivation in a medium containing a fatty acid are shown in Table 2.

TABLE 2

| | Addition concentration (%, w/v) | | | |
|---|---|---|---|---|
| Additive | 0 | 0.01 | 0.05 | |
| Control | 100/100 | — | — | 0.1 |
| myristic acid | | *a/*b | 200/100.6 | |
| | | 100/100.6 | | |
| palmitic acid | | 100/99.4 | 200/104.2 | |
| palmitoleic acid | | 100/77.3 | 200/111.3 | |
| oleic acid | | 200/103.0 | 200/103.6 | 200/108.9 |
| t-vaccenic acid | | 150/89.7 | 200/85.6 | |
| linoleic acid | | 100/98.2 | 200/106.6 | |
| arachidonic acid | | 200/80.4 | — | |
| sodium oleic acid | | | | 150/92.1 |

In the table, *a shows relative values based on the HSA production of control (cultivation without fatty acid) which is

Measurement of HSA concentration

The culture was sampled and after a 5 minute centrifugation at 15,000 rpm, the obtained culture supernatant was subjected to HSA measurement by a reversed passive hemagglutination test (RPHA) and the HSA concentration in the sample was calculated by comparison with a standard HSA sample (Miles).

Measurement of cell concentration

The culture was sampled, and after appropriate dilution with distilled water, the absorbance at 540 nm was measured spectrophotometer (Shimazu, UV 240).

As described hereinabove, the present invention increases HSA production by cultivating a host, obtained by genetic engineering, in a medium which has been supplemented with a higher fatty acid having 10 to 26 carbon atoms or its salt.

EXAMPLE 2

Cultivation of *Saccharomyces cerevisiae* AH22 transformed and capable of secretory expression of human serum albumin

*Saccharomyces cerevisiae* A124-35 (FERM BP-2527) was cultured in the following manner. A loopful of the abovementioned recombinant yeast grown on a plate comprising 0.7% yeast nitrogen base, 2% glucose and 3% Bacto-agar was inoculated into 50 ml of YNB medium (0.7% yeast nitrogen base and 2% glucose) and cultured at 30° C. for 2 days. The whole culture then was inoculated into 500 ml of YNB medium and cultured at 30° C. for 2 days. Cells were collected by centrifugation, suspended in 500 ml of YPG medium (YPG was prepared by dissolving 10 g of yeast extract and 20 g of Bacto-peptone in water to make 900 ml). The solution was autoclaved and when cooled, mixed with 100 ml of separately autoclaved 20% galactose) with 0.1 w/v % oleic acid and shake-cultured at 30° C. for 5 days. The HSA production multiplied 1.5 times that obtained by cultivation without oleic acid.

EXAMPLE 3

*Bacillus subtilis* transformed and capable of secretory expression of human serum albumin (see European Patent Publication No. 229712) was cultured in 10 ml of 2% yeast extract (Glfco) containing 50 µg/ml erythromycin and 0.1 w/v % oleic acid at 37° C. for 24 hours. The HSA production multiplied 2 times that obtained by cultivation without oleic acid.

EXAMPLE 4

*Pichia pastoris* GTS115 was transformed by a mutant $AOX_2$ promoter obtained by modifying the -255th base of the natural $AOX_2$ promoter [Yeast, vol. 5, 167-177 (1989)] from a T to C, to a obtain HSA-producing strain UHG42-3. This HSA-producing strain was inoculated into YPD medium, and cultured at 30° C. overnight. The culture obtained was inoculated into 50 ml of 2% MeOH-YP medium (0.5% yeast extract, 2% Bacto-peptone, 2% MeOH) at a concentration wherein the initial $OD_{540}$ was 0.1, and cultured at 30° C. for 3 days. As a result, the HSA production with 0.1 w/v % oleic acid multiplied 1.2 times that obtained by cultivation without oleic acid.

What is claimed is:

1. A method for producing human serum albumin which comprises cultivating a human serum albumin-producing yeast prepared by genetic engineering in a medium containing a fatty acid having 10 to 26 carbon atoms or its salt, wherein the fatty acid is added to the medium at a concentration of 0.005-0.4% (w/v).

2. A method for producing human serum albumin according to claim 1, wherein the fatty acid or its salt is selected from the group consisting of myristic acid, palmitic acid, palmitoleic acid, oleic acid, t-vaccenic acid, linoleic acid, arachidonic acid, and their salts.

3. A method for producing human serum albumin according to claim 1, wherein the yeast is selected from the group consisting of the genus Saccharomyces and the genus Pichia.

4. A method for producing human serum albumin according to claim 1, wherein the medium is a liquid medium.

5. A method for cultivating a human serum albumin-producing yeast prepared by genetic engineering, wherein the yeast is cultured in a medium containing a fatty acid having 10 to 26 carbon atoms or its salt in a concentration of 0.005-0.4% (w/v).

* * * * *